US009808428B2

(12) United States Patent
Gendelman et al.

(10) Patent No.: US 9,808,428 B2
(45) Date of Patent: Nov. 7, 2017

(54) COMPOSITIONS AND METHODS FOR THE DELIVERY OF THERAPEUTICS

(71) Applicant: The Board of Regents of the University of Nebraska, Lincoln, NE (US)

(72) Inventors: Howard E. Gendelman, Omaha, NE (US); Xin-Ming Liu, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/111,046

(22) PCT Filed: Jan. 14, 2015

(86) PCT No.: PCT/US2015/011364
§ 371 (c)(1),
(2) Date: Jul. 12, 2016

(87) PCT Pub. No.: WO2015/108945
PCT Pub. Date: Jul. 23, 2015

(65) Prior Publication Data
US 2016/0346222 A1 Dec. 1, 2016

Related U.S. Application Data

(60) Provisional application No. 61/927,315, filed on Jan. 14, 2014.

(51) Int. Cl.
*A61K 31/445* (2006.01)
*A61K 9/51* (2006.01)
*A61K 47/24* (2006.01)
*A61K 45/06* (2006.01)
*A61K 31/46* (2006.01)

(52) U.S. Cl.
CPC .......... *A61K 9/5153* (2013.01); *A61K 9/5123* (2013.01); *A61K 31/46* (2013.01); *A61K 45/06* (2013.01); *A61K 47/24* (2013.01)

(58) Field of Classification Search
CPC ............................ B82Y 10/00; C07D 401/04
USPC .......................................... 514/323; 977/774
See application file for complete search history.

(56) References Cited

U.S. PATENT DOCUMENTS

| 5,145,684 | A | 9/1992 | Liversidge et al. |
| 6,045,829 | A | 4/2000 | Liversidge et al. |
| 6,068,858 | A | 5/2000 | Liversidge et al. |
| 2002/0041898 | A1 | 4/2002 | Unger et al. |
| 2005/0048002 | A1 | 3/2005 | Rabinow et al. |
| 2006/0280430 | A1 | 12/2006 | Rabinow et al. |
| 2011/0236437 | A1 | 9/2011 | Destache |
| 2012/0039978 | A1 | 2/2012 | Moscona et al. |
| 2013/0236553 | A1 | 9/2013 | Gendelman et al. |
| 2015/0125401 | A1* | 5/2015 | Gendelman .......... A61K 9/5146 424/9.322 |

FOREIGN PATENT DOCUMENTS

| WO | 99/02665 | 1/1999 |
| WO | 2000/066090 | 11/2000 |
| WO | 2005/072706 | 8/2005 |
| WO | 2006/116764 | 11/2006 |
| WO | 2010/009075 | 1/2010 |
| WO | 2010/011814 | 1/2010 |
| WO | 2011/119566 | 9/2011 |
| WO | 2012/037320 | 3/2012 |
| WO | 2012/061480 | 5/2012 |
| WO | 2014/169207 | 10/2014 |

OTHER PUBLICATIONS

Nowacek, A.S., et al., "NanoART synthesis, characterization, uptake, release and toxicology for human monocyte-macrophage drug delivery" Nanomedicine (Lond) (2009) 4(8):903-17.
Arainga, M., et al., "Opposing regulation of endolysosomal pathways by long-acting nanoformulated antiretroviral therapy and HIV-1 in human macrophages" Retrovirology (2015) 12:5.
Puligujja, P., et al., "Pharmacodynamics of long-acting folic acid-receptor targeted ritonavir boosted atazanavir nanoformulations" Biomaterials (2015) 41:141-50.
Gautam, N., et al., "Pharmacokinetics, Biodistribution, and Toxicity of Folic Acid-Coated Antiretroviral Nanoformulations" Antimicrob. Agents Chemother. (2014) 58(12):7510-9.
Edagwa, B.J., et al., "Development of HIV Reservoir Targeted Long Acting Nanoformulated Antiretroviral Therapies" Curr Med Chem. (2014) 21(36):4186-4198.
Guo, D., et al., "Endosomal Trafficking of Nanoformulated Antiretroviral Therapy Facilitates Drug Particle Carriage and HIV Clearance" J. Virol. (2014) 88(17):9504-13.
Puligujja, P., et al., "Macrophage Folate Receptor-Targeted Antiretroviral Therapy Facilitates Drug Entry, Retention, Antiretroviral Activities and Biodistribution for Reduction of Human Immunodeficiency Virus Infections" Nanomedicine (2013) 9(8):1263-73.
Gautam, N., et al., "Preclinical Pharmacokinetics and Tissue Distribution of Long-Acting Nanoformulated Antiretroviral Therapy" Antimicrob. Agents Chemother. (2013) 57(7):3110-20.
Balkundi, S., et al., "Comparative manufacture and cell-based delivery of antiretroviral nanoformulations" Int. J. Nanomedicine (2011) 6:3393-404.
Mallipeddi, R., et al., "Progress in Antiretroviral Drug Delivery using Nanotechnology" Int. J. Nanomedicine (2010) 5:533-47.
Liu, Y., et al., "Folic acid conjugated nanoparticles of mixed lipid monolayer shell and biodegradable polymer core for targeted delivery of Docetaxel" Biomaterials (2010) 31:330-338.

* cited by examiner

*Primary Examiner* — Raymond Henley, III
(74) *Attorney, Agent, or Firm* — Robert C. Netter, Jr.; Dann, Dorfman, Herrell & Skillman

(57) ABSTRACT

The present invention provides compositions and methods for the delivery of antivirals to a cell or subject.

25 Claims, 4 Drawing Sheets

COMPOSITIONS AND METHODS FOR THE DELIVERY OF THERAPEUTICS

Figure 1:
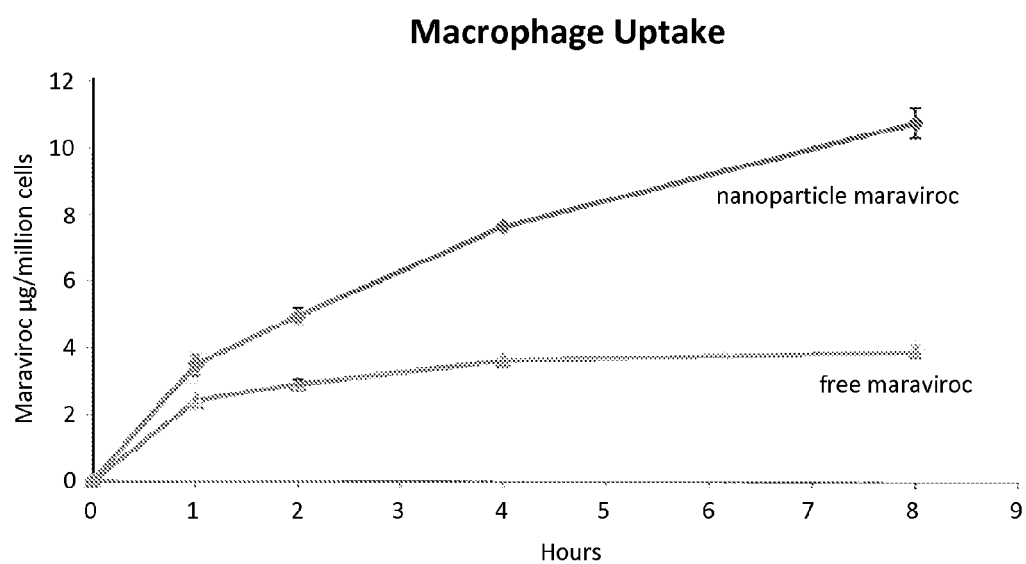

This application is a §371 application of PCT/US2015/011364, filed Jan. 14, 2015, which claims priority under 35 U.S.C. §119(e) to U.S. Provisional Patent Application No. 61/927,315, filed Jan. 14, 2014. The foregoing applications are incorporated by reference herein.

FIELD OF THE INVENTION

The present invention relates generally to the delivery of therapeutics. More specifically, the present invention relates to compositions and methods for the delivery of therapeutic agents to a patient for the treatment of a viral infection.

BACKGROUND OF THE INVENTION

The need to improve the bioavailability, pharmacology, cytotoxicities, and interval dosing of antiretroviral medications in the treatment of human immunodeficiency virus (HIV) infection is notable (Broder, S. (2010) Antivir. Res., 85:1-18; Este et al. (2010) Antivir. Res., 85:25-33; Moreno et al. (2010) J. Antimicrob. Chemother., 65:827-835). Since the introduction of antiretroviral therapy (ART), incidences of both mortality and co-morbidities associated with HIV-1 infection have decreased dramatically. However, many limitations associated with ART still remain which prevent full suppression of viral replication in HIV-infected individuals. These limitations include poor pharmacokinetics (PK) and biodistribution, life-long daily treatment, and multiple untoward toxic side effects (Garvie et al. (2009) J. Adolesc. Health 44:124-132; Hawkins, T. (2006) AIDS Patient Care STDs 20:6-18; Royal et al. (2009) AIDS Care 21:448-455). Since antiretroviral medications are quickly eliminated from the body and do not thoroughly penetrate all organs, dosing schedules tend to be complex and involve large amounts of drug. Patients have difficulty properly following therapy guidelines leading to suboptimal adherence and increased risk of developing viral resistance, which can result in treatment failure and accelerated progression of disease (Danel et al. (2009) J. Infect. Dis. 199:66-76). For HIV-infected patients who also experience psychiatric and mental disorders and/or drug abuse, proper adherence to therapy is even more difficult (Meade et al. (2009) AIDS Patient Care STDs 23:259-266; Baum et al. (2009) J. Acquir. Immune Defic. Syndr., 50:93-99). If dosing is not strictly maintained and consistent, virus can mutate and drug resistance will ultimately develop.

Accordingly, there is a need for drug delivery systems that optimize cell uptake and retention, improve intracellular stability, extend drug release, maintain antiretroviral efficacy, and minimize cellular toxicity within transporting cells.

SUMMARY OF THE INVENTION

In accordance with the instant invention, nanoparticles/nanoformulations comprising at least one therapeutic agent, at least one hydrophobic polymer, and at least one surfactant are provided. In a particular embodiment, the surfactant is a glycerophospholipid. In a particular embodiment, the hydrophobic polymer is poly (lactic-co-glycolic acid) (PLGA). In a particular embodiment, the surfactant is linked to at least one targeting ligand such as a macrophage targeting ligand (e.g., folate). An individual nanoparticle may comprise targeted and non-targeted surfactants. In a particular embodiment, the therapeutic agent is an antiviral, antiretroviral, or anti-HIV compound, particularly a CCR5 co-receptor antagonist.

In a particular embodiment, the nanoparticle of the instant invention comprises a CCR5 receptor antagonist (e.g., maraviroc), a hydrophobic polymer (e.g., PLGA), and a surfactant (e.g., glycerophospholipid, optionally conjugated to polyethylene glycol), optionally with a macrophage targeting ligand (e.g., folate).

Pharmaceutical compositions comprising at least nanoparticle of the instant invention and at least one pharmaceutically acceptable carrier are also provided.

According to another aspect of the instant invention, uses/methods for treating, inhibiting, or preventing a disease or disorder (e.g., a retroviral (e.g., HIV) infection) in a subject are provided. In a particular embodiment, the method comprises administering to the subject at least one nanoparticle/nanoformulation of the instant invention. In a particular embodiment, the methods are for treating, inhibiting, or preventing an HIV infection and the therapeutic agent of the nanoparticle is an anti-HIV compound, particularly a CCR5 co-receptor antagonist such as maraviroc. In a particular embodiment, the method further comprises administering at least one further therapeutic agent or therapy for the disease or disorder, e.g., at least one additional anti-HIV compound.

BRIEF DESCRIPTIONS OF THE DRAWING

FIG. 1 provides a graph of the microphage uptake of free maraviroc or nanoformulated maraviroc.

Figure 2:
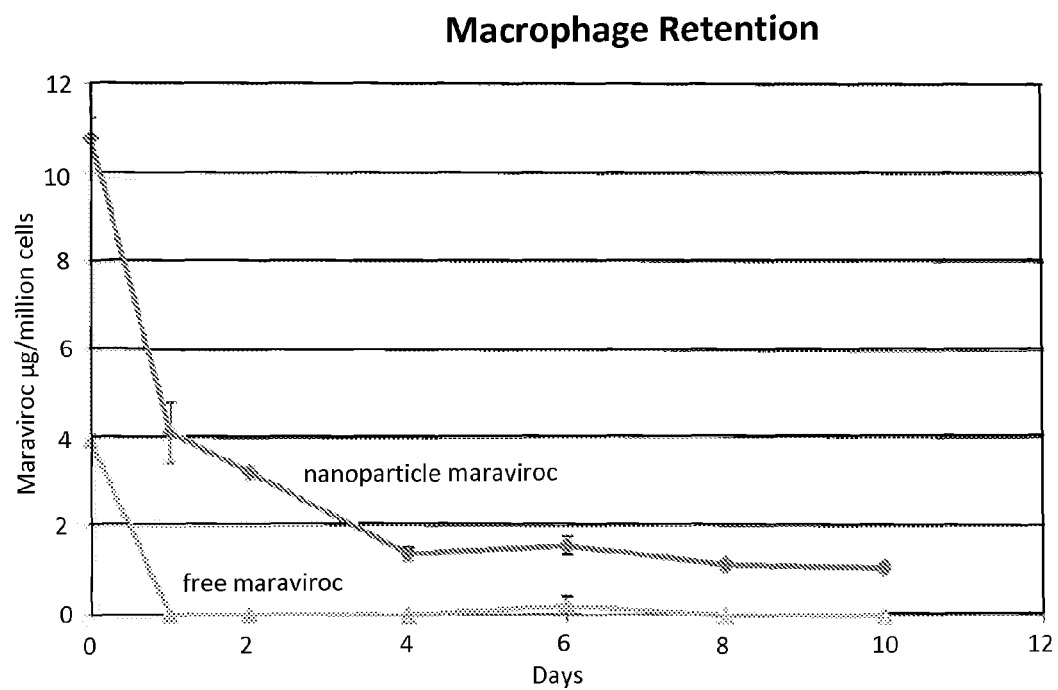

FIG. 2 provides a graph of the microphage retention of free maraviroc or nanoformulated maraviroc.

Figures 3A, 3B:
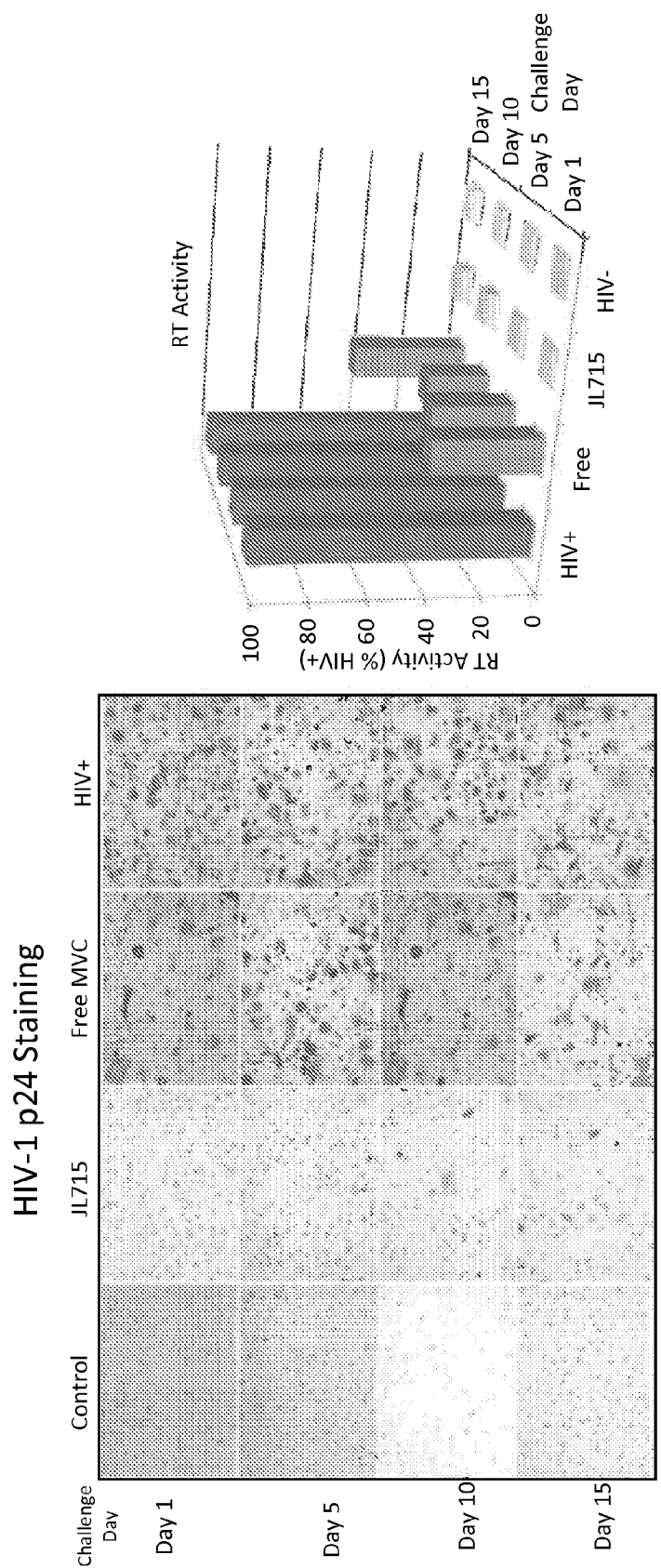

FIG. 3A provides images of cells stained for HIV-1 p24 after treatment with free maraviroc or nanoformulated maraviroc and HIV-1 infection. Control samples are without treatment and without infection. HIV+ samples are without treatment. FIG. 3B provides a graph of reverse transcription in negative control (HIV−), positive control (HIV+), free maraviroc treated (Free), and nanoformulated maraviroc treated (JL715) cells challenged with HIV-1 at the indicated day.

Figure 4:
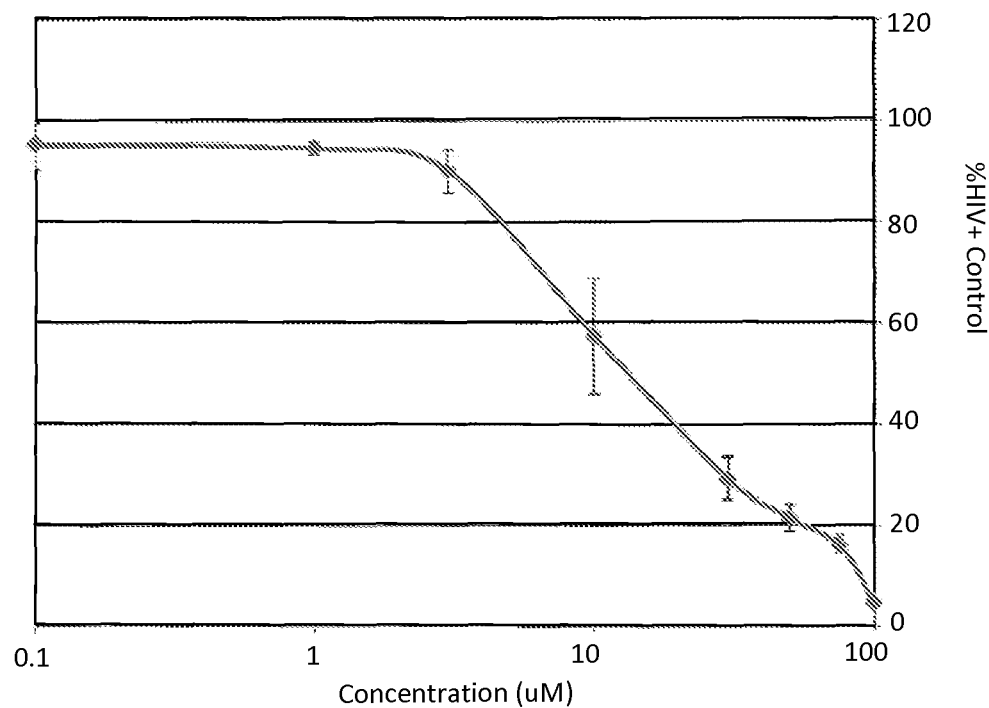

FIG. 4 provides a graph of the antiretroviral activity of nanoformulated maraviroc treated cells with variable drug concentrations and challenged with HIV-1 15 days after treatment.

DETAILED DESCRIPTION OF THE INVENTION

Antiretroviral therapy (ART) shows several limitations in adherence, pharmaceutics and effectiveness. Administrations commonly require life-long frequent daily dosing, substantive toxicities, and demonstrate limited access to tissue and cellular viral reservoirs. This precludes viral eradication efforts. As there are no current vaccination strategies for HIV eradication, alternative chemical vaccination strategies are desirable. To this end, the instant invention provides long-acting nanoparticles to improve patient adherence, reduce systemic toxicities, and reduce residual viral loads. Such long-acting HIV treatments will facilitate lower dosing intervals from daily to monthly or even yearly. The instant invention allows for ART for the long-term goal of HIV eradication. The invention may also be used as an efficient pre-exposure prophylaxis (PrEP) strategy.

Maraviroc (MVC; Selzentry®) is a CCR5 co-receptor antagonist commonly used as part of combination antiretroviral therapy (cART). The target is HIV-1 infected people with CCR5-tropic (R5) virus. When used with select antiretrovirals, the efficacy of MVC is significant and sustained. However, MVC has drawbacks and limitations that prevent maximal efficacy including: a twice-daily dosing regimen, limitations in virologic suppressive activity, and a lack of specific delivery to sites of viral entry.

To overcome the limitations associated with MVC, the drug was packaged into nanoparticles enabling monocyte-macrophage uptake and delivery. The creation of a cell-based drug depot facilitates particle dissolution and subsequent sustained release of MVC at its action site. As shown hereinbelow, polymeric lipid-coated poly (lactic-co-glycolic acid) (PLGA)-MVC nanoparticles were manufactured using a single emulsion-solvent evaporation technique. The physicochemical characteristics of nanoformulated MVC, as well as human monocyte-derived macrophage (MDM) uptake, retention, release and antiretroviral responses were examined. MDM treated with nanoformulated MVC (nMVC) or native MVC for 8 hours exhibited intracellular drug levels of 10.76 and 3.90 $\mu g/10^6$ cells, respectively. At one day or ten days following nMVC treatment (100 µM), MDM retained 1.06 µg MVC/$10^6$ cells while cells treated with free/native MVC had undetectable levels.

The antiretroviral activity was determined by reverse transcriptase (RT) activity and HIV-1 p24 antigen expression in HIV-1 infected MDM. MDM challenged with HIV-$1_{ADA}$>15 days after 8 hours of nMVC treatment exhibited dose dependent reductions in RT activity. At concentrations of 30-100 µM, nMVC and native MVC resulted in 95 and 22% RT activity reductions, respectively, compared to untreated infected cells. These results demonstrate that nMVC creates a cellular drug depot, which facilitates effective antiretroviral efficacy weeks after treatment. Overall, development of long acting targeted MVC, optionally together with reverse transcriptase, protease and/or integrase inhibitors leads to improved pharmacokinetics of cART and promote improved drug adherence and access.

The instant invention encompasses nanoparticles for the delivery of compounds to a cell. In a particular embodiment, the nanoparticle is for the delivery of antiretroviral therapy to a subject. The nanoparticles of the instant invention comprise at least one antiretroviral, at least one hydrophobic polymer, and at least one surfactant. These components of the nanoparticle, along with other optional components, are described hereinbelow.

Methods of synthesizing the nanoparticles/nanoformulations of the instant invention are known in the art. For example, the nanoparticle may be synthesized using, without limitation, an emulsion (e.g., single emulsion, double emulsion, emulsion-evaporation), milling (e.g., wet milling), homogenization (e.g., high pressure homogenization), particle replication in nonwetting template (PRINT) technology, and/or sonication techniques. In a particular embodiment, the nanoformulations are synthesized using an emulsion technique (e.g., a single emulsion-solvent evaporation technique).

In a particular embodiment, the surfactants are firstly chemically modified with targeting ligands (e.g., through a linker) and then mixed with non-targeted surfactants in certain molar ratios prior to formation of the nanoparticles comprising the therapeutic agent and hydrophobic polymer. Targeted nanoformulations (e.g., those using ligands with high molecular weight) may be developed through either physically or chemically coating or/and binding on the surface of surfactants coating the therapeutic agent and hydrophobic polymer complex.

The nanoparticles of the instant invention may be used to deliver any agent(s) or compound(s), particularly bioactive agents, particularly therapeutic agents or diagnostic agents such as antiviral compounds to a cell or a subject (including non-human animals). The nanoparticles of the instant invention comprise at least one therapeutic agent, particularly at least one antiretroviral. The nanoparticles may be crystalline (solids having the characteristics of crystals) or solid-state nanoparticles of the therapeutic agent.

In a particular embodiment, the resultant nanoparticle is up to about 1 µm in diameter. In a particular embodiment, the nanoparticle is about 100 nm to about 500 nm in diameter, particularly about 100-300 nm in diameter. The nanoparticles may be, for example, rod shaped, elongated rods, irregular, or round shaped. In a particular embodiment, the nanoparticles are round. The nanoparticles of the instant invention may be neutral or charged (positively or negatively).

The therapeutic agent may be hydrophobic, a water insoluble compound, or a poorly water soluble compound. For example, the therapeutic agent may have a solubility of less than about 10 mg/ml, less than 1 mg/ml, more particularly less than about 100 µg/ml, and more particularly less than about 25 µg/ml in water or aqueous media in a pH range of 0-14, particularly between pH 4 and 10, between pH 6 and 8, or about pH 7, particularly at 20° C.

In a particular embodiment, the therapeutic agent is an antiviral, more particularly an antiretroviral. The antiretroviral may be effective against or specific to lentiviruses. Lentiviruses include, without limitation, human immunodeficiency virus (HIV) (e.g., HIV-1, HIV-2), bovine immunodeficiency virus (BIV), feline immunodeficiency virus (FIV), simian immunodeficiency virus (SIV), and equine infectious anemia virus (EIA). In a particular embodiment, the therapeutic agent is an anti-HIV agent (e.g., anti-HIV-1 agent). In a particular embodiment, the therapeutic agent is a CCR5 receptor antagonist. CCR5 antagonists include, for example, maraviroc (Selzentry®, Celsentri) and vicriviroc. In a particular embodiment, the therapeutic agent is maraviroc.

An anti-HIV compound or an anti-HIV agent is a compound which inhibits HIV (e.g., inhibits HIV replication). Examples of anti-HIV agents include, without limitation:

(I) Nucleoside-analog reverse transcriptase inhibitors (NRTIs). NRTIs refer to nucleosides and nucleotides and analogues thereof that inhibit the activity of HIV-1 reverse transcriptase. An example of nucleoside-analog reverse transcriptase inhibitors is, without limitation, adefovir dipivoxil.

(II) Non-nucleoside reverse transcriptase inhibitors (NNRTIs). NNRTIs are allosteric inhibitors which bind reversibly at a nonsubstrate-binding site on the HIV reverse transcriptase, thereby altering the shape of the active site or blocking polymerase activity. Examples of NNRTIs include, without limitation, delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), rilpivrne (TMC278, Edurant™), DAPY (TMC120), BILR-355 BS, PHI-236, and PHI-443 (TMC-278).

(III) Protease inhibitors (PI). Protease inhibitors are inhibitors of the HIV-1 protease. Examples of protease inhibitors include, without limitation, darunavir, amprenavir (141W94, AGENERASE®), tipranivir (PNU-140690, APTIVUS®), indinavir (MK-639; CRIXIVAN®), saquinavir (INVIRASE®, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515.

(IV) Fusion or entry inhibitors. Fusion or entry inhibitors are compounds, such as peptides, which act by blocking HIV's entry in to the cell. For example, the inhibitor may block access to the cell receptors required for viral entry or may bind to HIV envelope protein and block the structural changes necessary for the virus to fuse with the host cell. Examples of fusion inhibitors include, without limitation, CCR5 receptor antagonists (e.g., maraviroc (Selzentry®, Celsentri), vicriviroc), enfuvirtide (INN, FUZEON®), T-(DP-178, FUZEON®) and T-1249.

(V) Integrase inhibitors. Integrase inhibitors are a class of antiretroviral drug designed to block the action of integrase, a viral enzyme that inserts the viral genome into the DNA of the host cell. Examples of integrase inhibitors include, without limitation, raltegravir, elvitegravir, and MK-2048.

Anti-HIV compounds also include maturation inhibitors (e.g., bevirimat). Maturation inhibitors are typically compounds which bind HIV gag and disrupt its processing during the maturation of the virus. Anti-HIV compounds also include HIV vaccines such as, without limitation, ALVAC® HIV (vCP1521), AIDSVAX®B/E (gp120), and combinations thereof. Anti-HIV compounds also include HIV antibodies (e.g., antibodies against gp120 or gp41), particularly broadly neutralizing antibodies.

More than one anti-HIV agent may be used, particularly where the agents have different mechanisms of action (as outlined above). In a particular embodiment, the anti-HIV therapy is highly active antiretroviral therapy (HAART). The therapeutic agents may be contained within the nanoparticle (e.g., with a CCR5 antagonist). In a particular embodiment, the nanoparticle comprises a CCR5 antagonist and the other anti-HIV agents are administered to the subject separately. For example, the other anti-HIV agents may be administered in separate compositions (e.g., comprising a pharmaceutically acceptable carrier). The other anti-HIV agents may be administered concurrently and/or sequentially with the nanoparticle of the instant invention.

The nanoparticles of the instant invention comprise at least one hydrophobic polymer. The hydrophobic polymer(s) and the therapeutic agent may form the core of the nanoparticles of the invention. Examples of hydrophobic polymers include, but are not limited to: poly(lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene). In a particular embodiment, the hydrophobic polymer is PLGA (e.g., PLGA 75:25). Notably, PLGA is hydrolyzed in the body to lactic acid and glycolic acid, which can be metabolized via the Krebs cycle, thereby minimizing toxicity.

As stated hereinabove, the nanoparticles of the instant invention comprise at least one surfactant. A "surfactant" refers to a surface-active agent, including substances commonly referred to as wetting agents, detergents, dispersing agents, or emulsifying agents. Surfactants are usually organic compounds that are amphiphilic. Generally, the surfactant will coat the hydrophobic core comprising the therapeutic agent and the hydrophobic polymer. In a particular embodiment, the weight ratio of hydrophobic polymer to surfactant is about 0.001 to about 1, particularly about 0.005 to about 0.8, about 0.01 to about 0.6, or about 0.02 to about 0.5.

Examples of surfactants include, without limitation, synthetic or natural phospholipids, pegylated lipids, polysorbates, poly(ethylene glycol)-co-poly(lactide-co-glycolide) (PEG-PLGA), their derivatives, ligand-conjugated derivatives and combinations thereof. Other surfactants and their combinations that can form stable nanoparticles or/and can chemically/physically bind to the targeting ligands of HIV infectable/infected CD4+ T cells, macrophages and dendritic cells can be used in the instant invention. Further examples of surfactants include, without limitation: 1) non-ionic surfactants (e.g., pegylated and/or polysaccharide-conjugated polyesters and other hydrophobic polymeric blocks such as poly(lactide-co-glycolide) (PLGA), polylactic acid (PLA), polycaprolactone (PCL), other polyesters, poly(propylene oxide), poly(1,2-butylene oxide), poly(n-butylene oxide), poly(tetrahydrofurane), and poly(styrene); glyceryl esters, polyoxyethylene fatty alcohol ethers, polyoxyethylene sorbitan fatty acid esters, polyoxyethylene fatty acid esters, sorbitan esters, glycerol monostearate, polyethylene glycols, polypropyleneglycols, cetyl alcohol, cetostearyl alcohol, stearyl alcohol, aryl alkyl polyether alcohols, polyoxyethylene-polyoxypropylene copolymers, poloxamines, cellulose, methylcellulose, hydroxylmethylcellulose, hydroxypropylcellulose, hydroxypropylmethylcellulose, polysaccharides, starch and their derivatives, hydroxyethylstarch, polyvinyl alcohol, polyvinylpyrrolidone, and their combination thereof); and 2) ionic surfactants (e.g., phospholipids, amphiphilic lipids, 1,2-dialkylglycero-3-alkylphophocholines, dimethylaminoethanecarbamoyl cheolesterol (DC-Chol), N-[1-(2,3-Dioleoyloxy)propyl]-N,N,N-trimethylammonium (DOTAP), alkyl pyridinium halides, quaternary ammonium compounds, lauryldimethylbenzylammonium, acyl carnitine hydrochlorides, dimethyldioctadecylammonium (DDAB), n-octylamines, oleylamines, benzalkonium, cetyltrimethylammonium, chitosan, chitosan salts, poly(ethylenimine) (PEI), poly(N-isopropyl acrylamide) (PNIPAM), and poly(allylamine) (PAH), poly (dimethyldiallylammonium chloride) (PDDA), alkyl sulfonates, alkyl phosphates, alkyl phosphonates, potassium laurate, triethanolamine stearate, sodium lauryl sulfate, sodium dodecylsulfate, alkyl polyoxyethylene sulfates, alginic acid, alginic acid salts, hyaluronic acid, hyaluronic acid salts, gelatins, dioctyl sodium sulfosuccinate, sodium carboxymethylcellulose, cellulose sulfate, dextran sulfate and carboxymethylcellulose, chondroitin sulfate, heparin, synthetic poly(acrylic acid) (PAA), poly (methacrylic acid) (PMA), poly(vinyl sulfate) (PVS), poly(styrene sulfonate) (PSS), bile acids and their salts, cholic acid, deoxycholic acid, glycocholic acid, taurocholic acid, glycodeoxycholic acid, and combinations thereof).

The surfactant of the instant invention may be charged or neutral. In a particular embodiment, the surfactant is neutral or negatively charged (e.g., poloxamers, polysorbates, phospholipids, and their derivatives). In a particular embodiment, the surfactant is an amphiphilic block copolymer. In a particular, embodiment, at least one surfactant of the nanoparticle is an amphiphilic block copolymer, particularly a copolymer comprising at least one block of poly(oxyethylene) and at least one block of poly(oxypropylene). In a particular embodiment, the surfactant is a poloxamer. Other biocompatible amphiphilic copolymers include those described in Gaucher et al. (J. Control Rel. (2005) 109:169-188).

In a particular embodiment, the surfactant is a phospholipid, particularly a glycerophospholipid. Examples of glycerophospholipids include, without limitation: 1,2-distearoyl-sn-glycero-3-phosphoethanolamine (DSPE), 1,2-distearoyl-sn-glycero-3-phosphocholine (DSPC), and 1,2-distearoyl-sn-glycero-3-phosphoglycerol (DSPG). The glycerophospholipid may be conjugated to a polymer (e.g., a hydrophilic polymer) such as a polyethylene glycol polymer or derivative thereof (e.g., methoxy poly(ethylene glycol)). The nanoparticles of the instant invention may comprise glycerophospholipids and glycerophospholipids conjugated to a hydrophilic polymer such as a polyethylene glycol polymer or derivative thereof. In a particular embodiment, the molar ratio of glycerophospholipids and glycerophospholipids conjugated to a hydrophilic polymer in the nanoparticles of the instant invention is from about 0.001 to 100%. In a particular embodiment, the molar ratio of glycerophospholipids and glycerophospholipids conjugated to a hydrophilic polymer is from about 1:1 to about 50:1, from about 2:1 to about 20:1, from about 5:1 to about 12:1, or about 8:1. In a particular embodiment, the nanoparticles of the instant invention comprise a glycerophospholipid conjugated to a hydrophilic polymer and a non-conjugated version of the glycerophospholipid. In a particular embodiment, the nanoparticle comprises DSPE, DSPC, and/or DSPG. In a particular embodiment, the nanoparticle comprises $DSPE_{MPEG}2000$, DSPC, and DSPG.

The surfactant of the instant invention may be linked to a targeting ligand. A targeting ligand is a compound that will specifically bind to a specific type of tissue or cell type. In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. The targeting ligand may be linked directly to the surfactant or via a linker. Generally, the linker is a chemical moiety comprising a covalent bond or a chain of atoms that covalently attaches the ligand to the surfactant. The linker can be linked to any synthetically feasible position of the ligand and the surfactant (e.g., the hydrophilic portion). Exemplary linkers may comprise at least one optionally substituted; saturated or unsaturated; linear, branched or cyclic alkyl group or an optionally substituted aryl group. The linker may also be a polypeptide (e.g., from about 1 to about 10 amino acids, particularly about 1 to about 5). The linker may be a synthetic hydrophilic polymer. The linker may be non-degradable and may be a covalent bond or any other chemical structure which cannot be substantially cleaved or cleaved at all under physiological environments or conditions.

The nanoparticles of the instant invention may comprise targeted and non-targeted surfactants. In a particular embodiment, the molar ratio of targeted and non-targeted surfactants in the nanoparticles of the instant invention is from about 0.001 to 100%. In a particular embodiment, the nanoparticles of the instant invention comprise a folate targeted surfactant and a non-targeted version of the surfactant.

The targeted nanoformulations of the instant invention may comprise a targeting ligand for directing the nanoparticles to HIV tissue and cellular sanctuaries/reservoirs (e.g., central nervous system, gut associated lymphoid tissues (GALT), CD4+ T cells, macrophages, dendritic cells, etc.). In a particular embodiment, the targeting ligand is a macrophage targeting ligand; CD4+ T cell targeting ligand, or a dendritic cell targeting ligand. Macrophage targeting ligands include, without limitation, folate receptor ligands (e.g., folate (folic acid) and folate receptor antibodies and fragments thereof (see, e.g., Sudimack et al. (2000) Adv. Drug Del. Rev., 41:147-162)), mannose receptor ligands (e.g., mannose), formyl peptide receptor (FPR) ligands (e.g., N-formyl-Met-Leu-Phe (fMLF)), and tuftsin (the tetrapeptide Thr-Lys-Pro-Arg). Other targeting ligands (e.g., for targeting HIV reservoirs) include, without limitation, hyaluronic acid, gp120, and ligands or antibodies specific for CD4, CCR5, CXCR4, CD7, CD111, CD204, CD49a, or CD29. The targeting of the nanoparticles (e.g., to macrophage) provides for superior targeting, decreased excretion rates, decreased toxicity, and prolonged half life compared to free drug or non-targeted nanoparticles.

The instant invention encompasses pharmaceutical compositions comprising at least one nanoparticle of the instant invention and at least one pharmaceutically acceptable carrier. As stated hereinabove, the nanoparticle may comprise more than one therapeutic agent. In a particular embodiment, the pharmaceutical composition comprises a first nanoparticle comprising a first therapeutic agent(s) and a second nanoparticle comprising a second therapeutic agent(s), wherein the first and second therapeutic agents are different. The pharmaceutical compositions of the instant invention may further comprise other therapeutic agents (e.g., other anti-HIV compounds (e.g., those described hereinabove)).

The nanoparticles of the instant invention may be used to treat a viral infection, particularly retroviral or lentiviral infections, particularly HIV (e.g., HIV-1) infections (e.g., a CCR5-dependent HIV). The present invention encompasses methods for preventing, inhibiting, and/or treating a viral infection, particularly retroviral or lentiviral infections, particularly HIV (e.g., HIV-1) infections (e.g., a CCR5-dependent HIV). The pharmaceutical compositions of the instant invention can be administered to an animal, in particular a mammal, more particularly a human, in order to treat/inhibit an HIV infection. The pharmaceutical compositions of the instant invention may also comprise at least one other antiviral agent, particularly at least one other anti-HIV compound/agent. The additional anti-HIV compound may also be administered in a separate pharmaceutical composition from the anti-HIV NPs of the instant invention. The pharmaceutical compositions may be administered at the same time or at different times (e.g., sequentially).

In a particular embodiment, the present invention features a use or method of treating or inhibiting an HIV infection by administration of nanoparticles comprising maraviroc, poly(lactic-co-glycolic acid), and glycerophospholipids and glycerophospholipids conjugated to polyethylene glycol. In a particular embodiment, the present invention features a use or method of preventing an HIV infection by administration of nanoparticles comprising maraviroc, poly(lactic-co-glycolic acid), and glycerophospholipids and glycerophospholipids conjugated to polyethylene glycol as surfactants.

The dosage ranges for the administration of the pharmaceutical compositions of the invention are those large enough to produce the desired effect (e.g., curing, relieving, treating, and/or preventing the HIV infection, the symptoms of it (e.g., AIDS, ARC), or the predisposition towards it). In a particular embodiment, the pharmaceutical composition of the instant invention is administered to the subject at an amount from about 5 µg/kg to about 500 mg/kg. In a particular embodiment, the pharmaceutical composition of the instant invention is administered to the subject at an amount greater than greater than about 0.5 mg/kg, greater than about 1 mg/kg, greater than about 5 mg/kg, or greater than about 50 mg/kg. In a particular embodiment, the pharmaceutical composition of the instant invention is administered to the subject at an amount from about 0.5 mg/kg to about 100 mg/kg, about 10 mg/kg to about 100 mg/kg, or about 15 mg/kg to about 50 mg/kg. The dosage should not be so large as to cause significant adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The nanoparticles described herein will generally be administered to a patient as a pharmaceutical composition. The term "patient" as used herein refers to human or animal subjects. These nanoparticles may be employed therapeutically, under the guidance of a physician.

The pharmaceutical compositions comprising the nanoparticles of the instant invention may be conveniently formulated for administration with any pharmaceutically acceptable carrier(s). For example, the complexes may be formulated with an acceptable medium such as water, buffered saline, detergents, suspending agents, or suitable mixtures thereof. The concentration of the nanoparticles in the chosen medium may be varied and the medium may be chosen based on the desired route of administration of the pharmaceutical composition. Except insofar as any conventional media or agent is incompatible with the nanoparticles to be administered, its use in the pharmaceutical composition is contemplated.

The dose and dosage regimen of nanoparticles according to the invention that are suitable for administration to a particular patient may be determined by a physician considering the patient's age, sex, weight, general medical condition, and the specific condition for which the nanoparticles are being administered and the severity thereof. The physician may also take into account the route of administration, the pharmaceutical carrier, and the nanoparticle's biological activity.

Selection of a suitable pharmaceutical composition will also depend upon the mode of administration chosen. For example, the nanoparticles of the invention may be administered by direct injection or intravenously. In this instance, a pharmaceutical composition comprises the nanoparticle dispersed in a medium that is compatible with the site of injection.

Nanoparticles of the instant invention may be administered by any method. For example, the nanoparticles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the nanoparticles are administered parenterally, intramuscularly, subcutaneously, or to the bloodstream (e.g., intravenously). Pharmaceutical compositions for injection are known in the art. If injection is selected as a method for administering the nanoparticle, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, suspensions, syrups, elixirs, dispersions and powders/granules for reconstitution. Dosage forms for topical administration include, without limitation, creams, gels, ointments, salves, patches and transdermal delivery systems.

Pharmaceutical compositions containing a nanoparticle of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. In a particular embodiment, the nanoformulations of the instant invention, due to their long-acting therapeutic effect, may be administered once every 0.5, 1, 2, 6, or 12 months or even less frequently. For example, the nanoformulations of the instant invention may be administered once every 0.5, 1, 2, 3, 4, 5, 6, 7, 8, 9, 10, 11, 12, 15, 18, 21, 24 or more months.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of nanoparticles may be determined by evaluating the toxicity of the molecules or cells in animal models. Various concentrations of nanoparticles in pharmaceutical composition may be administered to mice, and the minimal and maximal dosages may be determined based on the beneficial results and side effects observed as a result of the treatment. Appropriate dosage unit may also be determined by assessing the efficacy of the nanoparticle treatment in combination with other standard drugs. The dosage units of nanoparticle may be determined individually or in combination with each treatment according to the effect detected.

The pharmaceutical composition comprising the nanoparticles may be administered at appropriate intervals until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a pharmaceutical composition comprising a nanoparticle of the instant invention and, particularly, at least one pharmaceutically acceptable carrier. The instant invention also encompasses methods wherein the subject is treated via ex vivo therapy. In particular, the method comprises removing cells from the subject, exposing/contacting the cells in vitro to the nanoparticles of the instant invention, and returning the cells to the subject. In a particular embodiment, the cells comprise macrophage. Other methods of treating the disease or disorder may be combined with the methods of the instant invention may be co-administered with the pharmaceutical compositions of the instant invention.

The instant also encompasses delivering the nanoparticle of the instant invention to a cell in vitro (e.g., in culture). The nanoparticle may be delivered to the cell in at least one carrier.

Definitions

The following definitions are provided to facilitate an understanding of the present invention.

The singular forms "a," "an," and "the" include plural referents unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc. In a particular embodiment, the treatment of a retroviral infection results in at least an inhibition/reduction in the number of infected cells.

A "therapeutically effective amount" of a compound or a pharmaceutical composition refers to an amount effective to prevent, inhibit, treat, or lessen the symptoms of a particular disorder or disease. The treatment of a microbial infection (e.g., HIV infection) herein may refer to curing, relieving, and/or preventing the microbial infection, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

The term "antimicrobials" as used herein indicates a substance that kills or inhibits the growth of microorganisms such as bacteria, fungi, viruses, or protozoans.

As used herein, the term "antiviral" refers to a substance that destroys a virus or suppresses replication (reproduction) of the virus.

As used herein, the term "highly active antiretroviral therapy" (HAART) refers to HIV therapy with various combinations of therapeutics such as nucleoside reverse transcriptase inhibitors, non-nucleoside reverse transcriptase inhibitors, HIV protease inhibitors, and fusion inhibitors.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The following example provides illustrative methods of practicing the instant invention, and is not intended to limit the scope of the invention in any way.

Example

Polymeric lipid-coated poly (lactic-co-glycolic acid) (PLGA)-MVC nanoparticles were manufactured using a single emulsion-solvent evaporation technique (Liu et al. (2010) Biomaterials 31:330-338). Lipid-coated PLGA based nanoparticles containing PLGA (75:25) and 1,2-distearoyl-sn-glycero-3-phosphatidylethanolamine (DSPE) modified with methoxypoly(ethylene glycol) (mPEG) having a mean molecular weight of 2000 ($DSPE_{MPEG}2000$): 1,2-distearoyl-sn-glycero-3-phosphocholine (DSPC):1,2-distearoyl-sn-glycero-3-phosphoglycerol (DSPG) in a 1:7:0.7 molar ratio were synthesized (formula JL715). The drug loading in the nanoparticles is about 5% to about 20%. The weight ratio of phospholipid to PLGA is about 0.02-0.5. The resultant nanoparticles had an average particle size of 241.7 nm, a polydispersity index (PDI) of 0.217, and a zeta potential of −34.2. The physicochemical characteristics of nanoformulated MVC, as well as human monocyte-derived macrophage (MDM) uptake, retention, release and antiretroviral responses were examined. MDM treated with nanoformulated MVC (nMVC) or free MVC for 8 hours exhibited intracellular drug levels of 10.77 and 3.91 $\mu g/10^6$ cells, respectively (FIG. 1). Ten days following nMVC treatment (100 μM), MDM retained 1.07 μg $MVC/10^6$ cells while free MVC was undetectable (FIG. 2).

FIG. 3 shows the comparison of antiretroviral activity of nMVC and free maraviroc (MVC) as determined by HIV-1 p24 antigen expression (FIG. 3A) and reverse transcriptase (RT) activity (FIG. 3B). RT activity was determined by $^3$H-TTP incorporation in medium from cells loaded with nMVC or free MVC for 8 hours and then challenged with HIV-1$_{ADA}$ at 1, 5, 10, 15 days after treatment. As seen in FIG. 3, nMVC therapy led to dramatically reduced p24 expression and RT activity compared to the treatment with free MVC.

FIG. 4 shows the antiretroviral activity of nMVC as determined by reverse transcriptase (RT) activity. RT activity was determined by $^3$H-TIP incorporation in medium from cells loaded with nMVC for 8 hours and then challenged with HIV-1$_{ADA}$ 15 days after treatment. As seen in FIG. 4, nMVC significantly inhibited HIV-1 replication at concentrations below 100 μM as evidenced by the reduction in RT activity.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A nanoparticle consisting of at least one CCR5 receptor antagonist, at least one hydrophobic polymer, and at least one surfactant.

2. The nanoparticle of claim 1, wherein said hydrophobic polymer is poly(lactic-co-glycolic acid).

3. The nanoparticle of claim 1, wherein said surfactant is a glycerophospholipid.

4. The nanoparticle of claim 3, wherein said glycerophospholipid is selected from the group consisting of 1,2-distearoyl-sn-glycero-3-phosphoethanolamine (DSPE), 1,2-distearoyl-sn-glycero-3-phosphocholine (DSPC), and 1,2-distearoyl-sn-glycero-3-phosphoglycerol (DSPC).

5. The nanoparticle of claim 4, wherein said glycerophospholipid is conjugated to polyethylene glycol.

6. The nanoparticle of claim 1, wherein said CCR5 receptor antagonist is maraviroc.

7. A nanoparticle comprising at least one CCR5 receptor antagonist, at least one hydrophobic polymer, and at least one surfactant,
wherein said at least one surfactant is a mixture of 1,2-distearoyl-sn-glycero-3-phosphoethanolamine (DSPE), 1,2-distearoyl-sn-glycero-3-phosphocholine (DSPC), and 1,2-distearoyl-sn-glycero-3-phosphoglycerol (DSPG), wherein at least one of DSPE, DSPC, and DSPG is conjugated to polyethylene glycol.

8. The nanoparticle of claim 7, wherein said hydrophobic polymer is poly(lactic-co-glycolic acid).

9. The nanoparticle of claim 8, wherein said CCR5 receptor antagonist is maraviroc.

10. The nanoparticle of claim 7, wherein said at least one surfactant is a mixture of 1,2-distearoyl-sn-glycero-3-phosphatidylethanolamine (DSPE) modified with methoxypoly (ethylene glycol) (mPEG) having a mean molecular weight of 2000 (DSPE$_{MPEG}$2000), 1,2-distearoyl-sn-glycero-3-phosphocholine (DSPC), and 1,2-distearoyl-sn-glycero-3-phosphoglycerol (DSPG).

11. The nanoparticle of claim 10, wherein said hydrophobic polymer is poly(lactic-co-glycolic acid).

12. The nanoparticle of claim 11, wherein said CCR5 receptor antagonist is maraviroc.

13. The nanoparticle of claim 7, wherein said nanoparticle comprises a surfactant linked to at least one targeting ligand.

14. The nanoparticle of claim 13, wherein said targeting ligand is a macrophage targeting ligand.

15. The nanoparticle of claim 14, wherein said macrophage targeting ligand is folate.

16. The nanoparticle of claim 1, wherein said CCR5 receptor antagonist is maraviroc, wherein said hydrophobic polymer is poly(lactic-co-glycolic acid), wherein said surfactant is a glycerophospholipid, optionally conjugated to polyethylene glycol.

17. The nanoparticle of claim 16, wherein said glycerophospholipid is selected from the group consisting of 1,2-distearoyl-sn-glycero-3-phosphoethanolamine (DSPE), 1,2-distearoyl-sn-glycero-3-phosphocholine (DSPC), and 1,2-distearoyl-sn-glycero-3-phosphoglycerol (DSPG).

18. A pharmaceutical composition comprising at least one nanoparticle of claim 1 and at least one pharmaceutically acceptable carrier.

19. The pharmaceutical composition of claim 18, wherein said pharmaceutical composition further comprises at least one other anti-HIV compound.

20. A method for treating or inhibiting an HIV infection in a subject in need thereof, said method comprising administering to said subject a nanoparticle of claim 1.

21. The method of claim 20, further comprising the administration of at least one additional anti-HIV compound.

22. The nanoparticle of claim 1, wherein said at least one surfactant is a mixture of 1,2-distearoyl-sn-glycero-3-phosphoethanolamine (DSPE), 1,2-distearoyl-sn-glycero-3-phosphocholine (DSPC), and 1,2-distearoyl-sn-glycero-3-phosphoglycerol (DSPG), wherein at least one of DSPE, DSPC, and DSPG is conjugated to polyethylene glycol.

23. The nanoparticle of claim 22, wherein said hydrophobic polymer is poly(lactic-co-glycolic acid).

24. The nanoparticle of claim 23, wherein said CCR5 receptor antagonist is maraviroc.

25. The nanoparticle of claim 24, wherein said at least one surfactant is a mixture of 1,2-distearoyl-sn-glycero-3-phosphatidylethanolamine (DSPE) modified with methoxypoly (ethylene glycol) (mPEG) having a mean molecular weight of 2000 (DSPE$_{MPEG}$2000), 1,2-distearoyl-sn-glycero-3-phosphocholine (DSPC), and 1,2-distearoyl-sn-glycero-3-phosphoglycerol (DSPG).

* * * * *